(12) United States Patent
Barkai et al.

(10) Patent No.: US 10,064,976 B2
(45) Date of Patent: *Sep. 4, 2018

(54) MULTIPLE-LAYER IMMUNE BARRIER FOR DONOR CELLS

(71) Applicant: Beta-O2 Technologies Ltd., Rosh-Haayin (IL)

(72) Inventors: Uriel Barkai, MP Hof-Carmel (IL); Avi Rotem, Petach Tikva (IL); Yehezkel Bremer, Ra'anana (IL); Tova Neufeld, Ariel (IL)

(73) Assignee: Beta-O2 Technologies Ltd., Rosh-Haayin (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/430,064

(22) Filed: Feb. 10, 2017

(65) Prior Publication Data

US 2017/0151369 A1    Jun. 1, 2017

Related U.S. Application Data

(60) Continuation of application No. 15/233,119, filed on Aug. 10, 2016, now Pat. No. 9,566,366, which is a
(Continued)

(51) Int. Cl.
| | |
|---|---|
| *A61L 27/34* | (2006.01) |
| *A01N 1/02* | (2006.01) |
| *A61L 27/50* | (2006.01) |
| *C12N 5/00* | (2006.01) |
| *A61L 27/36* | (2006.01) |
| *A61L 27/56* | (2006.01) |

(Continued)

(52) U.S. Cl.
CPC ............ *A61L 27/00* (2013.01); *A01N 1/0231* (2013.01); *A61K 9/0024* (2013.01); *A61K 9/1652* (2013.01); *A61K 9/5073* (2013.01); *A61K 35/39* (2013.01); *A61L 27/20* (2013.01); *A61L 27/34* (2013.01); *A61L 27/36* (2013.01); *A61L 27/505* (2013.01); *A61L 27/56* (2013.01); *C12N 5/0012* (2013.01); *C12N 5/0676* (2013.01); *A61L 2400/18* (2013.01); *A61L 2420/02* (2013.01); *A61L 2420/08* (2013.01); *A61L 2430/40* (2013.01); *Y10S 623/915* (2013.01)

(58) Field of Classification Search
None
See application file for complete search history.

(56) References Cited

U.S. PATENT DOCUMENTS

| | | | | | |
|---|---|---|---|---|---|
| 5,578,314 | A | * | 11/1996 | Cochrum | A01N 1/02 264/4.1 |
| 6,372,244 | B1 | * | 4/2002 | Antanavich | A61F 2/022 424/422 |
| 2002/0022016 | A1 | * | 2/2002 | Walsh | A61K 9/1652 424/93.1 |

* cited by examiner

*Primary Examiner* — Bethany P Barham
*Assistant Examiner* — Dominic Lazaro
(74) *Attorney, Agent, or Firm* — Greenberg Traurig, LLP

(57) ABSTRACT

A system is provided, including a plurality of donor cells and a first alginate structure that encapsulates the plurality of donor cells. The first alginate structure has a guluronic acid concentration of between 64% and 74%. The system additionally includes a second alginate structure that surrounds the first alginate structure, the second alginate structure having a mannuronic acid concentration of between 52% and 60%. A selectively-permeable membrane is coupled at least in part to the second alginate structure. Other embodiments are also described.

14 Claims, 4 Drawing Sheets

Related U.S. Application Data division of application No. 13/153,721, filed on Jun. 6, 2011, now Pat. No. 9,446,168.

(60) Provisional application No. 61/351,992, filed on Jun. 7, 2010.

(51) Int. Cl.
*A61L 27/00* (2006.01)
*A61K 9/00* (2006.01)
*A61K 9/50* (2006.01)
*A61K 35/39* (2015.01)
*A61L 27/20* (2006.01)
*A61K 9/16* (2006.01)
*C12N 5/071* (2010.01)

MULTIPLE-LAYER IMMUNE BARRIER FOR DONOR CELLS

CROSS-REFERENCES TO RELATED APPLICATIONS

The present application is a divisional of U.S. patent application Ser. No. 13/153,721, which was filed on, Jun. 6, 2011, which was filed concurrently with PCT Patent Application PCT/IL2011/000445 on, Jun. 6, 2011, both of which claim priority to U.S. Provisional Application 61/351,992 filed on, Jun. 7, 2010. This application is also related to U.S. National Phase patent application Ser. No. 12/996,592, filed on Jan. 13, 2011, which claims priority to PCT Patent Application PCT/IL2009/000905, filed on Sep. 16, 2009, which claims priority to U.S. Provisional Patent Application 61/192,412 filed on Sep. 17, 2008, all of which are incorporated herein by reference.

FIELD OF THE INVENTION

Some applications of the present invention relate in general to implantation of donor cells in a recipient. More specifically, some applications of the present invention relate to optimization of implantation of donor cells using a multiple-layer immune barrier.

BACKGROUND

Oxygen is essential to many physiological and metabolic processes, including aerobic metabolism. A lack of oxygen for implanted cells often leads to cell injury or death. Oxygen provision is a vital component in sustaining transplanted cells.

The success of many transplants is compromised not only due to graft-host rejections, but also by ischemic conditions generated by insufficient oxygen supply to the transplant. Following implantation of the cells, oxygen can be provided to the implanted cells from the body tissue (mainly via diffusion). However, the relatively low ambient oxygen tension and the low natural diffusion rate are unable to provide highly metabolic cells with a significant, necessary amount of oxygen amount.

Islet transplantation is a clinical protocol aiming to help diabetes type I (DTI) patients. Transplanted cells, no matter their origin, elicits inflammatory and rejection reactions. To ensure engraftment and long-term survival of transplanted islets, medical approaches to such engraftment should target and address both (1) long-term rejection processes of the host against the graft, and (2) the initial inflammatory reaction of the host against the graft.

In order to achieve stable graft function, donor tissue should be provided with sufficient level of oxygen and should be protected from host immune and inflammatory cells and from their released toxic substances.

SUMMARY OF EMBODIMENTS

For some applications of the present invention, a multi-layer encapsulation barrier is provided which encapsulates a plurality of donor cells in order to protect and immunoisolate the donor cells in a body of a recipient. Typically, the donor cells comprise either allogeneic or xenogeneic cells of tissue or cells (e.g., functional cells, typically, islets of Langerhans) that are transplanted and immunoisolated by the artificial barrier. The multi-layer barrier comprises a first alginate hydrogel structure that macroencapsulates the plurality of islets and has a guluronic acid concentration of between 64% and 74%. The multi-layer barrier comprises a second alginate structure that surrounds the first alginate structure and has a mannuronic acid concentration of between 52% and 60%. The multi-layer barrier also comprises one semi-permeable membrane with pore size of less than 0.5 microns, e.g., a Biopore™ membrane, which reduces fibrosis and prevents direct contact between donor cells and host immune cells thus further immunoisolates the islets encapsulated in the multi-layer immune barrier.

The multi-layer barrier is configured so as to (a) eliminate cell-to-cell contact, thereby preventing T-cell mediated cytotoxicity against the encapsulated tissue, (b) minimize diffusion rates of larger molecules through the layers of the barrier and toward the cells encapsulated in the first alginate structure, and (c) provide for a greater distance for smaller molecules (i.e., cytokines and reactive organic substances (ROS)) to travel between cells which synthesize these smaller molecules and the islets that are encapsulated within the first, inner alginate structure.

The multi-layer immune barrier is formed so as to have a planar, geometric configuration, e.g., a slab, a sheet, or a disc. Typically, the multi-layer immune barrier has at least one substantially flat surface. The first alginate structure comprises an ultrapure grade alginate with high percent of guluronic acid (i.e., MVG Pronova, Norway) and a defined composition that is cross-linked with a divalent cation (i.e., Strontium) and encapsulates the cells or tissue segments in a hydrogel. Typically, the first alginate structure houses islets at densities of 1500-6000 islets/cm^2 of the first alginate structure, typically, about 4000 islets/cm^2 of the first alginate structure. The islets are positioned in the center of the first alginate structure, i.e., the islets encapsulated by the first alginate are surrounded by a thick layer of the first alginate. This central location of the islets with respect to the first alginate layer physically isolates and distances the islets from the surface of the multi-layer immune barrier.

Typically, the apparatus comprises a source of oxygen, or an oxygen supply (e.g., a vessel comprising air, another mixture of gases, or pure oxygen), that is coupleable to the multi-lumen barrier, and oxygen is actively supplied to the islets in the barrier by the source of oxygen. In such applications, the multi-lumen barrier is disposed within a housing, e.g., a scaffold, and the source of oxygen is coupleable to the housing. For some applications of the present invention, the multi-layer immune barrier is implanted in a well-perfused area of the body of the recipient in order to allow for sufficient oxygen to flow toward the islets that are encapsulated within the multi-layer immune barrier. For some applications of the present invention, the multi-layer immune barrier is implanted subcutaneously. The multi-layer immune barrier may be implanted independently of the source of oxygen.

There is therefore provided, in accordance with some applications of the present invention apparatus, including:

a plurality of donor cells;

a first alginate structure that encapsulates the plurality of donor cells, the first alginate structure having a guluronic acid concentration of between 64% and 74%;

a second alginate structure that surrounds the first alginate structure, the second alginate structure having a mannuronic acid concentration of between 52% and 60%; and a selectively-permeable membrane coupled at least in part to the second alginate structure.

In some applications of the present invention, the selectively-permeable membrane surrounds the second alginate structure.

In some applications of the present invention, the selectively-permeable membrane is embedded at least in part within the second alginate structure.

In some applications of the present invention, the guluronic acid concentration of the first alginate structure is between 67% and 71%.

In some applications of the present invention, the mannuronic acid concentration of the second alginate structure is between 54% and 58%.

In some applications of the present invention, the plurality of donor cells include cells of pancreatic islets.

In some applications of the present invention, the first alginate structure has a thickness of 300-700 um.

In some applications of the present invention, the first alginate structure has a thickness of 400-700 um.

In some applications of the present invention, the first alginate structure has a thickness of 500 um.

In some applications of the present invention, the first alginate structure has a thickness of 600 um.

In some applications of the present invention, the first alginate structure has a dry matter content of at least 1.8%.

In some applications of the present invention, the first alginate structure has a dry matter content of at least 2.2%.

In some applications of the present invention, the first alginate structure has a dry matter content of between 1.8 and 4.2%.

In some applications of the present invention, the dry matter content of the first alginate structure is between 2.2 and 4.0%.

In some applications of the present invention, the first alginate structure has a dry matter content of between 1.8 and 3.0%.

In some applications of the present invention, the dry matter content of the first alginate structure is between 2.2 and 2.6%.

In some applications of the present invention, the second alginate structure has a dry matter content of between 3.0 and 7.0%.

In some applications of the present invention, the dry matter content of the second alginate structure is between 5.5 and 6.5%.

In some applications of the present invention, the second alginate structure has a dry matter content of between 3.0 and 5.0%.

In some applications of the present invention, the dry matter content of the second alginate structure is between 3.5 and 4.5%.

In some applications of the present invention, the plurality of donor cells include cells that are disposed in a plurality of pancreatic islets, and the first alginate structure encapsulates that plurality of pancreatic islets at a density of between 1000 and 6500 islet equivalents (IEQ) per square cm.

In some applications of the present invention, the plurality of donor cells include cells that are disposed in a plurality of pancreatic islets, and the first alginate structure encapsulates that plurality of pancreatic islets at a density of between 1500 and 6000 islets per square cm.

In some applications of the present invention, the first alginate structure encapsulates that plurality of pancreatic islets at a density of between 3500 and 4500 islets per square cm.

In some applications of the present invention, the second alginate structure has an inner surface that is in contact with an outer surface of the first alginate structure, the apparatus has an external surface that is not in contact with the first alginate structure, and a distance between the inner surface of the second alginate structure and the external surface of the apparatus is between 25 um and 50 um.

In some applications of the present invention, the membrane is embedded within the second alginate structure, and the second alginate structure has an outer surface thereof which defines the external surface of the apparatus.

In some applications of the present invention, a distance from an external surface of the apparatus to a center of the first alginate structure is 300-500 um.

In some applications of the present invention, the distance from the external surface of the apparatus to the center of the first alginate structure is 350 um.

In some applications of the present invention, the distance from the external surface of the apparatus to the center of the first alginate structure is 300 um.

In some applications of the present invention, the membrane is embedded within the second alginate structure, and the second alginate structure has an outer surface thereof which defines the external surface of the apparatus.

In some applications of the present invention, the selectively-permeable membrane has a pore size of up to 0.2 um.

There is additionally provided, in accordance with some applications of the present invention, a method for encapsulating a plurality of donor cells, including:

encapsulating the plurality of donor cells in a first alginate structure having a guluronic acid concentration of between 64% and 74%;

surrounding the first alginate structure by a second alginate structure having a mannuronic acid concentration of between 52% and 60%; and surrounding the second alginate structure by a selectively-permeable membrane.

In some applications of the present invention, the guluronic acid concentration of the first alginate structure is between 67% and 71%, and surrounding the plurality of donor cells in the first alginate structure includes surrounding the plurality of cells in the first alginate structure having the guluronic acid concentration of between 67% and 71%.

In some applications of the present invention, the mannuronic acid concentration of the second alginate structure is between 54% and 58%, and surrounding the first alginate structure by the second alginate structure includes surrounding the first alginate structure by the second alginate structure having the mannuronic acid concentration of between 54% and 58%.

In some applications of the present invention, the plurality of donor cells include cells that are disposed in a plurality of pancreatic islets, and encapsulating the plurality of donor cells in the first alginate structure includes encapsulating the plurality of pancreatic islets in the first alginate structure at a density of between 1000 and 6500 islet equivalents (IEQ) per square cm.

In some applications of the present invention, the plurality of donor cells include cells that are disposed in a plurality of pancreatic islets, and encapsulating the plurality of donor cells in the first alginate structure includes encapsulating the plurality of pancreatic islets in the first alginate structure at a density of between 1500 and 6000 islets per square cm.

In some applications of the present invention, encapsulating the plurality of pancreatic islets in the first alginate structure includes encapsulating the plurality of pancreatic islets in the first alginate structure at a density of between 3500 and 4500 islets per square cm.

There is also provided, in accordance with some applications of the present invention, apparatus, including:

a plurality of donor cells;

a first alginate structure that encapsulates the plurality of donor cells, the first alginate structure having a distance from an outer surface thereof to a center of the first alginate structure, the distance being configured so as to attenuate diffusion toward the plurality of donor cells of molecules;

a second alginate structure that surrounds the first alginate structure, the second alginate structure having a structural composition selected so as to restrict passage therethrough of molecules having a molecular weight above and including 150 kDa; and a selectively-permeable membrane coupled at least in part to the second alginate structure, the membrane being configured to restrict passage therethrough of cells.

In some applications of the present invention, the first alginate structure is configured so as to attenuate diffusion toward the plurality of donor cells of negatively-charged molecules.

In some applications of the present invention, the second alginate structure has an inner surface that is in contact with an outer surface of the first alginate structure, the apparatus has an external surface that is not in contact with the first alginate structure, and a distance between the inner surface of the second alginate structure and the external surface of the apparatus is between 25 um and 50 um.

In some applications of the present invention, the membrane is embedded within the second alginate structure, and the second alginate structure has an outer surface thereof which defines the external surface of the apparatus.

In some applications of the present invention, the membrane is embedded within the second alginate structure, and the second alginate structure has an outer surface thereof which defines the external surface of the apparatus.

The present invention will be more fully understood from the following detailed description of applications thereof, taken together with the drawing, in which:

DETAILED DESCRIPTION OF THE EMBODIMENTS

Figure 1:
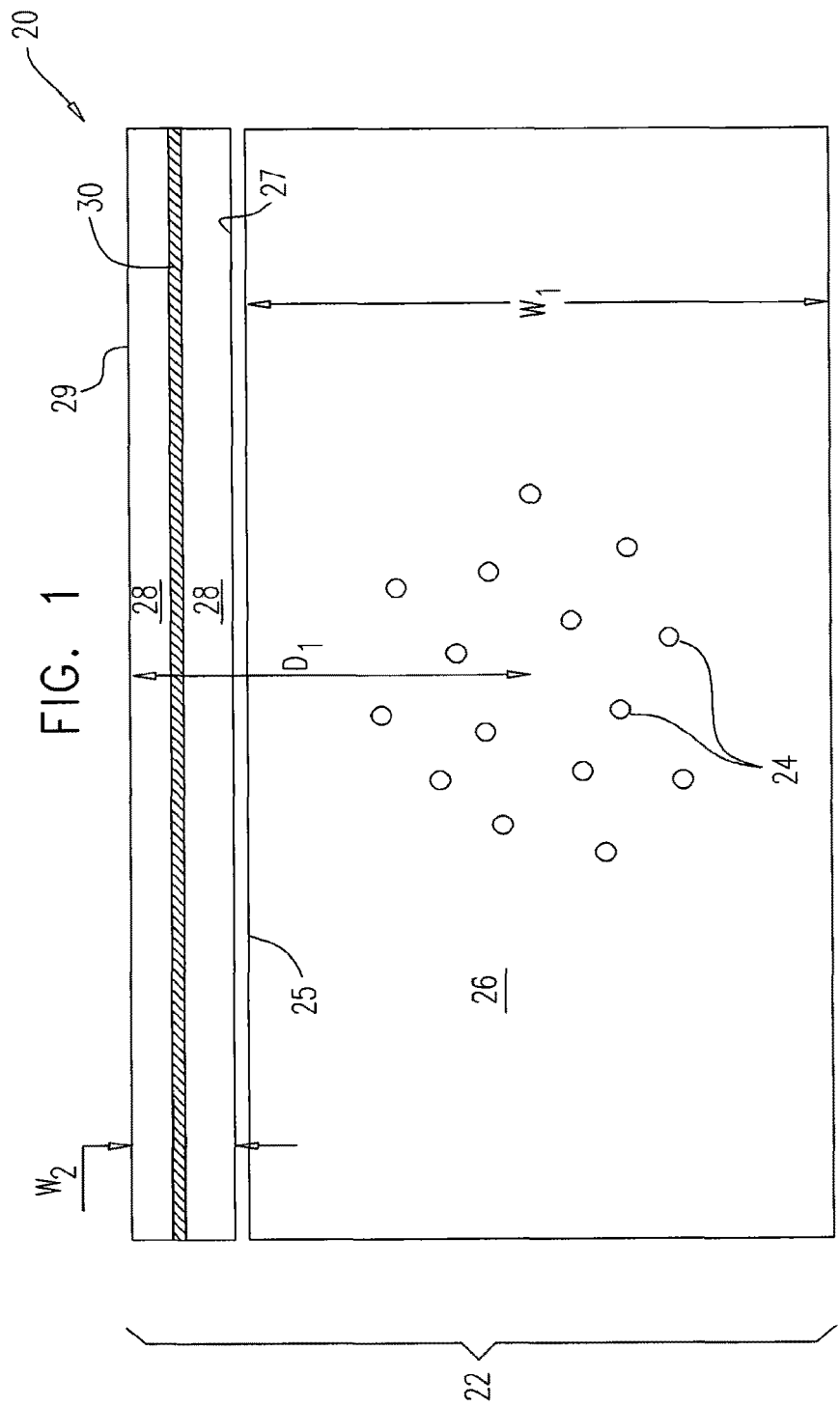
FIG. 1 is a schematic illustration of a multi-layer immune barrier having an inner first alginate structure that encapsulates a plurality of donor cells, in accordance with some applications of the present invention.

Reference is now made to FIG. 1, which is a schematic illustration of a system 20 comprising a multi-layer immune barrier 22, in accordance with some applications of the present invention. Multi-layer immune barrier 22 comprises a first, inner alginate hydrogel layer 26 which encapsulates a plurality of donor cells and/or tissue 24.

Typically, cells and/or tissue 24 comprise a plurality of islets of Langerhans. First, inner alginate layer has a guluronic acid concentration of between 64% and 74%, e.g., between 67% and 71%. Multi-layer immune barrier 22 further comprises a second, outer alginate structure 28 that surrounds at least in part (e.g., entirely, as shown) first, inner alginate structure 26. Second alginate structure has a mannuronic acid concentration of between 52% and 60%, e.g., between 54% and 58%.

For some applications, first alginate structure 26 has a dry matter content of at least 1.8%, e.g., at least 2.2%. For example, the first alginate structure may have a dry matter content of between 1.8 and 4.2%, such as between 2.2 and 4.0%.

For some applications, first alginate structure 26 has a dry matter content of between 1.8 and 3.0%, e.g., typically between 2.2 and 2.6%. First alginate structure 26 is typically cross-linked with a divalent cation, e.g., Strontium. Typically, second alginate structure 28 has a dry matter content of between 3.0 and 7.0%, e.g., between 5.5 and 6.5%. For some applications, second alginate structure 28 has a dry matter content of between 3.0 and 5.0%, e.g., typically between 3.5 and 4.5% and is crossed-linked with a divalent cation, e.g., Barium.

Typically, at least one semi-permeable membrane 30 is coupled to second, outer alginate structure 28 of barrier 22. Typically, membrane 30 comprises a Biopore™ membrane of approximately 25 um thickness. Membrane 30 may comprise silicone or hydrophilized Teflon, by way of illustration and not limitation. Membrane 30 reduces fibrosis and further immunoisolates the islets encapsulated in first alginate structure 26. Typically, the Biopore™ membrane 30 is embedded, or integrated within the alginate of second, outer alginate structure 28. For some applications of the present invention two or more membranes 30 (e.g., Biopore™, a Teflon™ membrane, or equivalent having a pore size of 0.25 um each) are impregnated within one or more alginate structures 28. Membrane 30 has a width of between 25 and 75 um. The two of more membranes/alginate structure(s) are placed one on top of the other to further restrict passage of constituents therethrough. Typically, as described hereinbelow, a plurality of first alginate structure 26 are disposed within an implantable housing, and second alginate structure 28 are coupled to a cover which covers the housing.

High-M alginate of second-outer alginate structure 28 is layered on either side of membrane 30. The alginate hydrogel of second, outer alginate structure is cross-linked by immersing the membrane-alginate system in 20-60 mM Barium chloride solution (e.g., typically 30 mM) for a period of 5-60 min (e.g., typically 12-16 min). As a result, second, outer alginate layer 28 comprises a membrane-alginate layer, wherein membrane 30 comprises a physical porous membrane in which the pores of membrane 30 are filled with cross-linked, high M, alginate.

Membrane 30 has a thickness of up to 25 um and a pore size of up to 0.5 um, e.g., 0.2 um. As described hereinabove, one or more membranes 30 is incorporated, embedded, or disposed within second, outer alginate structure 28. For other applications, membrane 30 surrounds second alginate structure 28 at an outer surface thereof.

The primary role of membrane 30 of multi-layer immune barrier 22 is to prevent cell-cell contact between donor cells 24 contained within first, inner alginate structure 26 and host cytotoxic T-cells. Thus, a direct effect of killing of donor cells 24 by the host cytotoxic cells is prevented.

Second, outer alginate structure 28 that surrounds first alginate structure 26 comprises a relatively high percentage mannuronic acid and is typically cross-linked with Barium. For some applications, second alginate structure 28 is cross-linked with Strontium or with Calcium. Additionally, second alginate structure 28 has a dry matter content of at least 3%. Taking together the properties of second alginate structure 28 (i.e., the high mannuronic acid concentration, the crosslinking of the alginate with Barium, and the increased dry matter concentration), it is hypothesized by the inventors that second alginate structure 28 significantly reduces the diffusion rates of macromolecules and large proteins, e.g., immunoglobulins and complement members, and their ability to pass through toward the islets that are encapsulated in first, inner alginate structure 26. Typically, these macromolecules have molecular weight structures which range between 150 kDa and 1500 kDa, e.g., between 150 kDa and 900 kDa. For example, second alginate structure restricts passage toward cells 24 of IgG having a molecular weight of approximately 150 kDa, a complement member having a molecular weight of up to 400 kDa, and of IgM which has a molecular weight of over 750 kDa.

Typically, second alginate structure 28 attenuates inward diffusion of immunoglobulin IgG (150 kDa), complement members C3 and C5 (190 kDa Each) and prevents the diffusion of complement C1 (400 kDa) and IgM (750 kDa), thereby prevents damage to cells associated with activation of the complement system.

The permeability properties of second alginate structure 28 were determined by considering the size, molecular weight, shape, and charge of the proteins that are designated to be restricted by second alginate structure 28. That is, second alginate structure 28 defines a pore size of 18 nm or lower. Additionally, second alginate structure 28 provides (a) obstructions which increase the path length for diffusion of molecules and polymer chains thorough the alginate, and (b) residual, polar, and hydrophobic charges which interact with the molecules and polymer chains diffusing through the alginate.

Alternatively, second alginate structure 28 comprises a medium guluronic acid concentration of between 47-57% and short G-blocks (i.e., chains of guluronic acid comprising fewer than 15 consecutive guluronic acid residues).

For either application in which second alginate structure 28 comprises a high mannuronic acid concentration or a medium guluronic acid concentration, as described hereinabove, second alginate structure 28 imparts biocompatibility to multi-layer immune barrier 22 because it reduces the innate immune response of inflammatory cells which are typically attracted to alginates having a high percentage of guluronic acid concentration (i.e., a high G-content). Therefore, it is hypothesized by the inventors that by increasing the percentage of mannuronic acid and/or by reducing the percentage of guluronic acid concentration of second alginate structure 28 (i.e., the alginate structure adjacent an external surface 29 of multi-layer immune barrier 22), the innate immune response against multi-layer immune barrier 22 is reduced. Additionally, membrane 30 prevents passage of immune cells (e.g., macrophages, neutrophils, antigen presenting cells, etc.) of the recipient through second alginate structure 28 and thereby through first alginate structure 26.

Under physiological conditions, the alginates of second alginate structure 28 and first alginate structure 26 are negatively charged. Additionally, under physiological conditions (e.g., physiological pH), most proteins are also negatively charged. Therefore, (a) in response to charge-charge interaction between the alginate and the proteins (e.g., chemokines and cytokines like IL-1 beta, TNF alpha, and interferon gamma) of the recipient, the inward diffusion through the alginate of proteins of the recipient will be attenuated, and in some cases, substantially eliminated, while (b) outward diffusion of proteins, e.g., insulin, from the encapsulated islets will be accelerated.

In such a manner, multi-layer immune barrier 22 functions as a membrane to immunoisolate the transplanted islets, and thus, the recipient mammal does not need to undergo immunosuppression (e.g., via administration of a drug) prior to and following implantation. Additionally, the electrical attraction/repulsion of the particles passing through the alginate supplements the immunoisolation properties of the alginate slab.

As described hereinabove, multi-layer immune barrier 22 has an external surface 29 thereof. For application in which membrane 30 is embedded within second alginate structure 28, an outer surface of second alginate structure 28 defines external surface 29 of multi-layer immune barrier 22. Second alginate structure 28 surrounds first alginate structure 26 in a manner in which multi-layer immune barrier 22 has a thickness or width W2 of between 30 um and 60 um, e.g., 50 um, between external surface 29 of multi-layer immune barrier 22 and inner surface 27 of second alginate structure 28.

Typically, surface 29 is generally smooth.

First alginate structure 26 has an outer surface 25 thereof that is in contact with inner surface 27 of second, outer alginate structure 28.

It is to be noted that the scope of the present invention includes the placement of membrane 30 between outer surface 25 of first alginate structure 26 and inner surface 27 of second, outer alginate structure 28.

Figure 2:
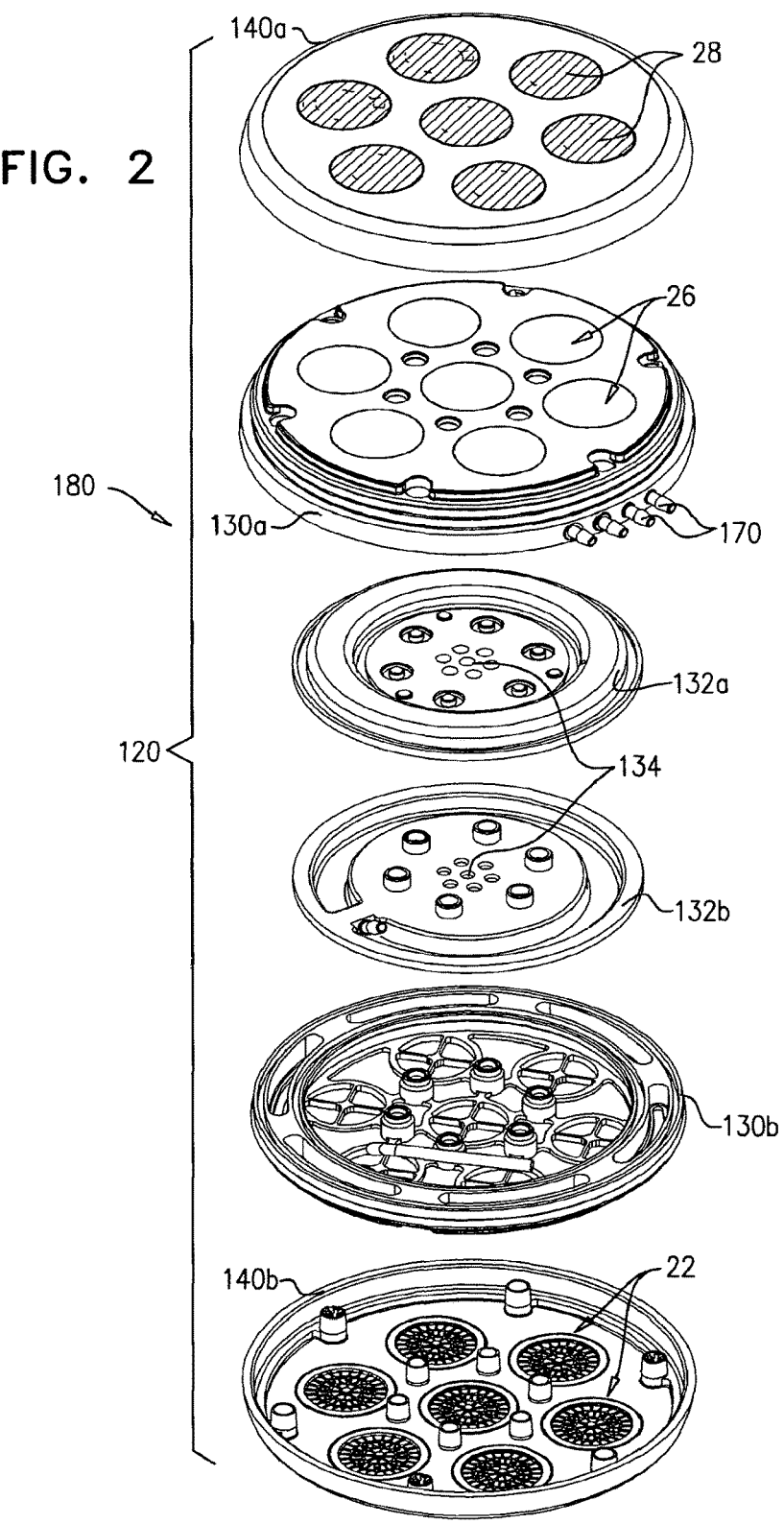
FIG. 2 is a schematic illustration of a plurality of multi-layer immune barriers coupled to a housing, in accordance with some applications of the present invention.
Figure 3:
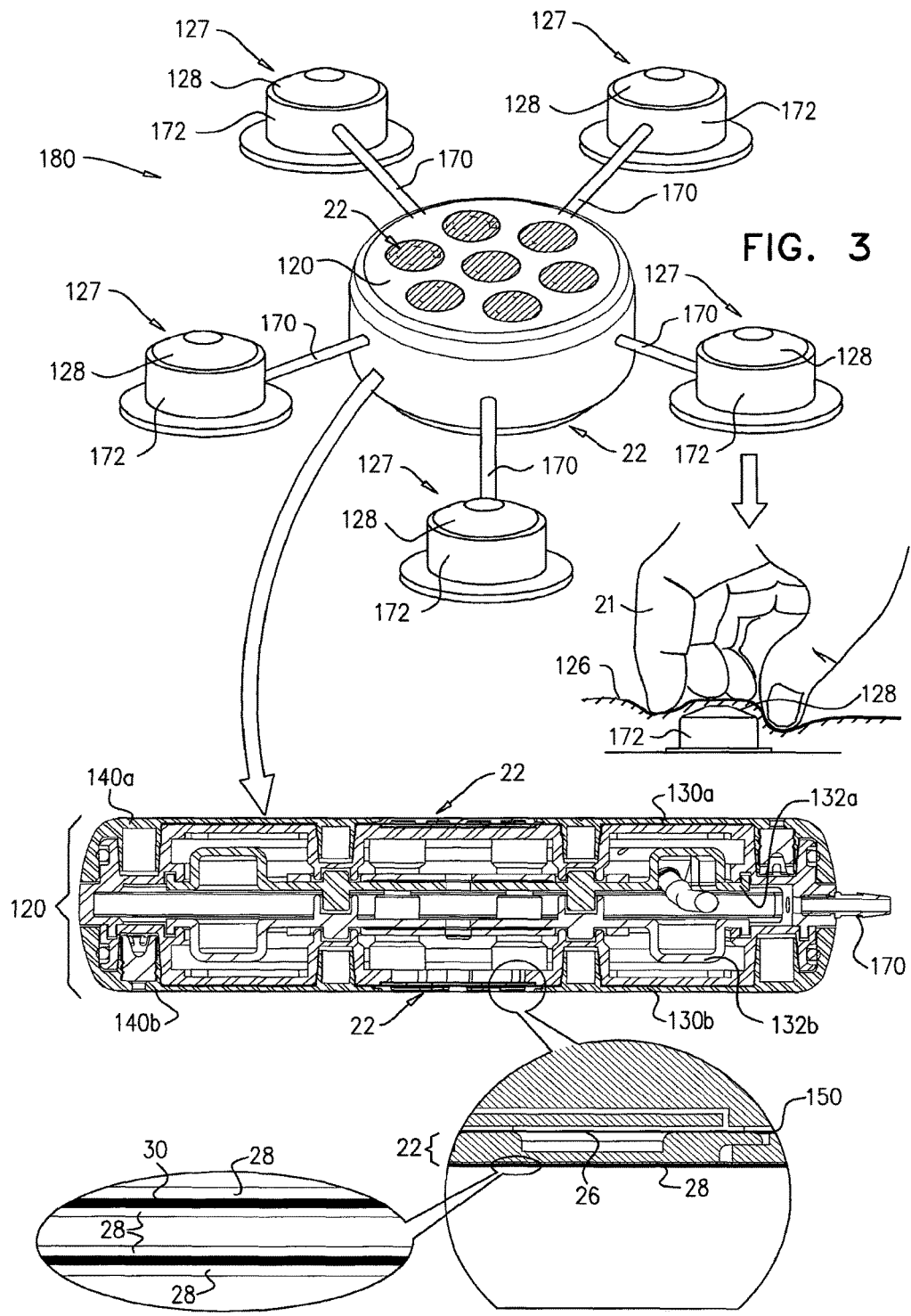
FIG. 3 is a schematic illustration of the housing of FIG. 2 couplable to a source of oxygen, in accordance with some applications of the present invention.

Reference is now made to FIGS. 2 and 3, which are schematic illustrations of a subcutaneously-implantable device 180 comprising a housing 120 which supports one or more multi-lumen barriers 22, in accordance with some applications of the present invention. Typically, housing 120 is configured for implantation in an animal that is non-human, e.g., a pig. Housing 120 comprises an upper housing element 130a and a lower housing element 130b. Upper and lower housing elements 130a and 130b comprise a biocompatible material (e.g., polyether ether ketone (PEEK)). Each housing element 130a and 130b are shaped to define a plurality of wells which each support a respective one of a plurality of first alginate structures 26 which hold the plurality of islets.

Housing 120 is coupled to one or more (e.g., a plurality) oxygen-delivering tubes 170 which facilitate provision of oxygen to the islets in alginate structures 26 within housing 120. Tubes 170 are in fluid communication with an oxygen reservoir which is surrounded by a reservoir housing having an upper oxygen reservoir housing element 132a and a lower oxygen reservoir housing element 132b which provide a space for oxygen to be stored from tubes 170. Oxygen reservoir housing elements 132a and 132b are each shaped so as to define a plurality of holes 134 for passage of oxygen therethrough and toward first alginate structures 26 which hold the islets. Oxygen reservoir housing elements 132a and 132b comprise plastic which is covered with silicone to regulate the oxygen provision. Housing 120 facilitates housing and provision of oxygen in a concentration of between 40% and 95% e.g., 95%, at a pressure of between 1 atm and 2 atm, (e.g. 1.35 atm), on a daily basis.

Housing 120 also comprises an upper cap 140a and a lower cap 140b which are coupled to upper and lower housing elements 130a and 130b, respectively. Each cap 140a and 140b is coupled to (e.g., glued to) one or more second alginate structures 28 (which each contain a respective membrane 30, as described hereinabove). Each second alginate structure 28 is aligned with a respective first alginate structure 26. Typically, first alginate structures 26 are assembled upon a metal scaffold, as shown in the image of lower cap 140b. Taken together, first alginate structures 26 and the respective second alginate structure 28 aligned therewith, form respective multi-layer immune barriers 22, as shown in the image of lower cap 140b.

As shown in FIG. 2, housing 120 holds fourteen multi-lumen immune barriers 22. It is to be noted that housing 120 may hold any number of barriers 22, e.g., between 1 and 20 barriers. The islets (shown as cells and/or tissue 24) encapsulated within first alginate structure 26 are typically disposed within a center of first alginate structure 26. Each one of the plurality of first alginate structures 26 is configured so as to encapsulate between 1500 and 6000 islets per square cm, e.g., typically, between 3500 and 4500 islets, and has an area of approximately 1 cm^2, by way of illustration and not limitation. For some applications, each one of the plurality of first alginate structures 26 is configured so as to encapsulate between 1000 and 6500 islet equivalents (IEQ) per square cm. First alginate structure 26 has a thickness, or width W1 of between 300 um and 700 um, e.g., between 400 um and 700 um, e.g., 500 um or 600 um. Multi-layer immune barrier 22 is typically coin- or disc-shaped. Typically, the first alginate structure 26 has a total surface area of 1 cm^2.

That is, for embodiments in which housing 120 comprises 14 slabs, as shown (e.g., for embodiments in which housing 120 is implanted in a pig or a human), housing 120 contains a total density of between 21,000 and 84,000 islets/cm^2, e.g., 28,000 islets/cm^2.

Figure 4:
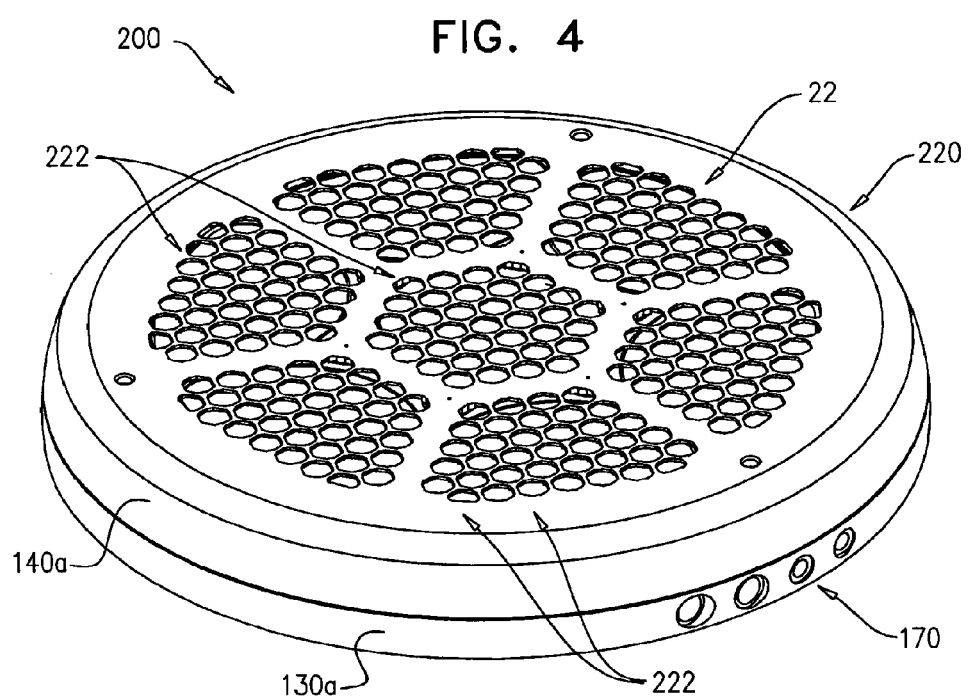
FIG. 4 is a schematic illustration of a subcutaneously-implantable housing for holding one or more multi-layer immune barriers, in accordance with some other applications of the present invention.

Reference is now made to FIG. 4, which is a schematic illustration of a subcutaneously-implantable device 200 comprising a housing 220 which supports one or more multi-lumen barriers 22, in accordance with some applications of the present invention. Typically, housing 220 is configured for implantation in human and is identical to housing 120, as described herein, with the exceptions as described herein. Housing 220 facilitates implantation of islets at a higher density than housing 120. Housing 220 holds a total density of up to 450,000 islets/cm^2 each alginate structure 26 is disposed in one or more slabs at upper housing element 130a and lower housing element 130b. Each slab has a surface area of approximately 100 cm^2 and holds islets at a density of 3000-6000 e.g., 4500 islets/cm^2. For some applications of the present invention, each housing element 130a and 130b holds one slab barrier 22 that is divided into one or more subcomponents 222 (e.g., a plurality, as shown) each having a surface area of between 1 and 100 cm^2.

It is to be noted that FIG. 4 shows only upper housing element 130a and upper cap 140a for clarity of illustration, and that the bottom half of housing 200 is identical to the upper half of housing 220, as shown and described herein.

Reference is now made to FIGS. 2-4. For applications in which housing 120 is configured for implantation in a pig (FIGS. 2-3), housing 120 has a height of 15-20 mm (e.g., 17 mm), and an outer diameter of 60-70 mm (e.g., 68 mm). For applications in which housing 220 is configured for implantation in a human (FIG. 4), housing 220 has a height of 15-40 mm (e.g., 25 mm) and an outer diameter of 70-120 mm (e.g., 90 mm).

For some applications, when each immune barrier 22 contains islets at a density of 3000 islets/cm^2, a plurality of slab-bearing inserts are used in order to form barrier 22 into a slab shape.

Typically, first alginate structure 26 encapsulates islet at densities ranging from 1500 to 6000 per square cm. Each islet has an average diameter of 124 um and a calculated volume of 1 nl. For example, when first alginate structure 26 encapsulates islets at a density of 3000 islets/cm^2 barrier 22 has a volume density (v/v) of 6% and, the footprint (that is, the surface are of the islets relative to the surface area of alginate structure 26) of 36%.

Taking together the dimensions of first alginate structure 26 and second alginate structure 28, multi-layer immune barrier 22 defines a distance D1 between external surface 29 thereof and the center of first alginate structure 26 of between 240 um and 320 um, e.g., between 260 um and 300 um. For some applications, the distance from the external surface to the center of first alginate structure is 300-500 um, e.g., 300 um-350 um. That is, for embodiments in which the islets are disposed substantially in a vicinity of the center of first alginate structure 26, multi-layer immune barrier 22 provides a relatively large traveling distance for molecules having a very low molecular weight and short half-life (e.g., reactive oxygen species (ROS), nitric oxide (NO) or $H_2O_2$). Since a majority of distance D1 is provided by first alginate structure 26, first alginate structure 26 functions to help attenuate and, in some cases, eliminate, the diffusion of these molecules toward the encapsulated islets.

Nitric oxide (NO) is a short-living molecule having a life-span of approximately 2-4 seconds and can travel only short distances away from its site of synthesis. The effective travelling distance of NO is defined as the distance within which its concentration is greater than the equilibrium dissociation constant of its target enzyme (guanylyl cyclase). This distance is estimated at 100-250 um. Taking into consideration that NO is produced by neutrophils and macrophages, multi-layer immune barrier 22 provides a defense strategy against NO by increasing the effective distance between these cells and the donor islets encapsulated within first alginate structure 26. Firstly, this distance is increased by (1) minimizing adhesion of inflammatory cells onto alginate surfaces (i.e., as described hereinabove by reducing the G-content of the alginate adjacent to external surface 29 of multi-layer immune barrier 22), (2) restricting passage of NO-producing cells through membrane 30, and (3) increasing the diffusion path between NO-producing cells and donor islets (i.e., by multi-layer immune barrier 22 which defines distance D1 between external surface 29 thereof and the center of first alginate structure 26).

Multi-layer immune barrier 22 restricts passage of cytokines responsively to the electrostatic repulsion forces of alginate structures 26 and 28. Width W1 of first alginate structure 26 (FIG. 1) provides a larger area for electrostatic forces to act upon the cytokines as they diffuse through first alginate structure 26.

Additionally, since first alginate structure 26 has a relatively high guluronic acid concentration, first alginate structure 26 imparts flexibility to multi-layer immune barrier 22.

FIG. 3 shows subcutaneously-implantable device 180 coupled to ports 172 which facilitate active provision of oxygen to cells and/or tissue 24 disposed within multi-layer barrier 22, in accordance with some applications of the present invention. As shown, housing 120 supports one or more (e.g., a plurality of) multi-layer immune barriers 22. Housing 120 is coupled to a plurality of fluid-injection ports 172. Ports 172 are disposed remotely from housing 120 and are coupled thereto by respective tubes 170 (tubes 170 are coupled to housing 120 as shown either in FIG. 2 or 3). The remote positioning of ports 172 with respect to housing 120 facilitates the delivery of fluid to housing 120 without substantially shifting the position of housing 120. An upper surface of each port comprises a penetrable surface 128, which functions as an oxygen delivery interface 127. Tube 170 facilitates transfer of oxygen from ports 172 to an oxygen reservoir 42 within housing 120 and toward multi-layer immune barriers 22 encapsulating the islets.

As shown, a user 21 grips a portion of skin 126 that lies over one of ports 172. The user penetrates penetrable surface 128, typically with a needle. A source of oxygen (not shown), e.g., a vessel such as a syringe, comprising a source of fluid which comprises oxygen, is coupled to the needle and supplies via the needle fluid containing oxygen to the islets that are disposed within multi-lumen barriers 22. In some applications of the present invention, the source of oxygen comprises air. Alternatively, the source of oxygen comprises pure oxygen.

In some applications of the present invention, the source of oxygen comprises a plurality of gases including oxygen. The gases are disposed in the container at a pressure of 1 atm or higher (e.g., 1.35 atm). Typically, the source of oxygen comprises around 5% carbon dioxide in order to maintain a balance of concentrations of carbon dioxide inside the housing and outside the housing. For some applications, the source of oxygen comprises a fluid comprising oxygen carriers (e.g., hemoglobin-based oxygen carriers such as chemically-modified hemoglobin, or "microbubbles" which comprise fluorocarbons such as dodecafluoropentane or perfluorodecalin) that are loaded with oxygen prior to the injection of the carriers into housing 120. The carriers facilitate the transport into housing 120 of a larger volume of compressed oxygen.

Oxygen reservoir housing 132 defines a space having a volume of between 75 ml and 300 ml, e.g., between 100 ml and 150 ml. Oxygen reservoir housing 132 comprises foam, e.g., an open-cell silicone foam, or simply an air gap which functions as a gas reservoir within the device. Reservoir 42 functions as a conduit for oxygen diffusion to the functional cells, as well as a reservoir for storing excess oxygen that is supplied to the housing by the source of oxygen. Techniques described herein with respect to oxygen reservoir housing 132 may be practiced in combination with techniques described with respect to an air gap in PCT Patent Application PCT/IL08/001204 to Stern et al., which is incorporated herein by reference.

In some applications of the present invention, housing 120 comprises the oxygen carriers. In such applications, the oxygen carriers function to store, or carry, oxygen when in excess, and release the oxygen upon a need therefore.

As shown in the enlarged cross-sectional image, each multi-layer immune barrier is coupled to two layers of second alginate structure 28, wherein a respective membrane 30 is embedded within each alginate structure 28. It is to be noted that any number of alginate structures 28 and membranes 30 may be used.

A respective gas-permeable membrane 150 is disposed between each alginate structure 26 and housing elements 130 to facilitate passage of oxygen from oxygen reservoir housing 132 to the islets disposed in each alginate structure 26 of each multi-lumen barrier 22.

Housing 120 is shown as being disc-shaped by way of illustration and not limitation. For example, housing 120 may be rectangular or any other suitable shape suitable for implantation under skin 126 of the recipient. In some embodiments, housing 120 is shaped to provide a plurality of projections which project radially from housing 120 and toward a vicinity of the body of the recipient which includes vasculature. In such applications, the projections function as oxygen delivery interface 127 by providing increased surface area of housing 120 for facilitating transport of oxygen from surrounding vasculature toward housing 120. For some applications, the projections of housing 120 contain the oxygen carriers, which store excess oxygen that has been absorbed into housing 120 by the projections.

At some time following implantation of housing 120 in the body of the recipient, housing 120 is primed with a suitable amount of oxygen-containing fluid. (The housing may have previously been filled with oxygen-containing fluid, as well.)

Techniques for active oxygen provision may be practiced together with any one of the techniques described in U.S. patent application Ser. No. 12/315,102 to Stern et al., entitled, "Apparatus for transportation of oxygen to implanted cells," filed on Nov. 26, 2008, which is incorporated herein by reference.

The scope of the present invention includes the encapsulation of cells and/or tissue 24 in multi-layer immune barrier 22 other than the plurality of islets, as described herein. That is, cells and/or tissue 24 which are encapsulated in multi-layer immune barrier 22 include cells found in pancreatic islets (e.g., beta cells, alpha cells, other pancreatic islet cells), hepatic cells, hepatocytes, neural and neuroendocrine cells, renal cortex cells, vascular endothelial cells, thyroid cells, parathyroid cells, adrenal cells (e.g., chromaffin cells), thymic cells, adrenal cells, ovarian cells, genetically-engineered cells, cloned cells, stem, cells, and/or testicular cells.

Additionally, techniques described herein may be performed in combination with techniques described in one or more of the following patent application, all of which are incorporated herein by reference:

US Patent Application Publication 2004/0133188 to Vardi et al., entitled, "Implantable device," filed Mar. 12, 2004;

US Patent Application Publication 2005/0136092 to Rotem et al., entitled, "Implantable device," filed Nov. 30, 2004;

US Patent Application Publication 2009/0012502 to Rotem et al., entitled, "Oxygen supply for cell transplant and vascularization," filed Jun. 4, 2008;

PCT Publication WO 09/031154 to Stern and Rozy, entitled, "Air gap for support cells," filed Sep. 7, 2008;

US Patent Application Publication 2010/0047311 to Rotem et al., entitled, "Protecting algae from body fluids," filed Jul. 31, 2009;

PCT Publication WO 10/032242 to Barkai et al., entitled, "Optimization of alginate encapsulation," filed Sep. 16, 2009; and/or PCT Publication WO 10/061387 to Stern et al., entitled, "Apparatus for transportation of oxygen to implanted cells," filed Nov. 25, 2009.

For some applications of the present invention, techniques described herein are practiced in combination with techniques described in one or more of the references cited in the Background or Cross-references sections of the present patent application.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An implantable device comprising:
    a housing; and
    a multi-layer immune barrier supported by the housing, wherein the multi-layer immune barrier comprises:
        a barrier layer, the barrier layer including a selectively-permeable hydrophilized membrane having pores impregnated with a cross-linked hydrogel; and
        a tissue layer positioned adjacent to the barrier layer, the tissue layer including a plurality of cells,
    wherein the housing comprises a cover, wherein the tissue layer is disposed within the housing, and the barrier layer is coupled to the cover.

2. The implantable device of claim 1, wherein the plurality of cells is selected from the group consisting of beta cells, alpha cells, hepatic cells, hepatocytes, neural cells, neuroendocrine cells, renal cortex cells, vascular endothelial cells, thyroid cells, parathyroid cells, adrenal cells, thymic cells, adrenal cells, ovarian cells, genetically-engineered cells, cloned cells, stem cells and testicular cells.

3. The implantable device of claim 1, wherein the plurality of cells comprises cells of pancreatic islets.

4. The implantable device of claim 1, wherein the tissue layer has a thickness of 300-700 microns.

5. The implantable device of claim 1, wherein the tissue layer includes a hydrogel encapsulating the plurality of cells.

6. The implantable device of claim 5, wherein the tissue layer has a dry matter content of at least 1.8%.

7. The implantable device of claim 1, wherein the barrier layer has a dry matter content of between 3.0 and 7.0%.

8. The implantable device of claim 1, wherein the selectively-permeable hydrophilized membrane has a pore size of up to 0.5 microns.

9. The implantable device of claim 1, wherein the plurality of cells comprises cells that are disposed in a plurality of pancreatic islets, and wherein the tissue layer encapsulates the plurality of pancreatic islets at a density of at least 1000 islet equivalents (IEQ) per square cm.

10. The implantable device of claim 1, wherein the plurality of cells comprises cells that are disposed in a plurality of pancreatic islets, and wherein the tissue layer encapsulates the plurality of pancreatic islets at a density of at least 1500 islets per square cm.

11. The implantable device of claim 1, further comprising:
    a gas reservoir;
    a gas permeable membrane positioned between the gas reservoir and the tissue layer;
    and one or more gas delivery tubes in fluid communication with the gas reservoir,
    wherein the gas reservoir is a space within the housing configured to receive gas from the gas delivery tubes and store the gas.

12. The implantable device of claim 11, further comprising:
    a plurality of fluid-injection ports disposed remotely from the housing, and coupled to the housing by respective gas delivery tubes, the fluid-injection ports comprising at least in part a penetrable surface for receiving a needle therethrough, and configured to receive a gas including oxygen from a source of the gas, and to facilitate passage of the gas to the plurality of cells while the housing is disposed within a body of a subject.

13. An implantable device comprising:
    a housing;
    a multi-layer immune barrier supported by the housing, wherein the multi-layer immune barrier comprises:
        a barrier layer, the barrier layer including a selectively-permeable hydrophilized membrane having pores impregnated with a cross-linked hydrogel; and
        a tissue layer positioned adjacent to the barrier layer, the tissue layer including a plurality of pancreatic islet cells,
    wherein the housing comprises a cover, wherein the tissue layer is disposed within the housing, and the barrier layer is coupled to the cover;
    a gas reservoir for storing a gas including oxygen within the housing;
    a gas permeable membrane positioned between the gas reservoir and the tissue layer;
    one or more gas delivery tubes in fluid communication with the gas reservoir; and
    a plurality of fluid-injection ports disposed remotely from the housing, and coupled to the housing by respective gas delivery tubes, the fluid-injection ports comprising at least in part a penetrable surface for receiving a needle therethrough, and configured to receive the gas from a source of the gas, and to facilitate passage of the gas to the plurality of pancreatic islet cells while the housing is disposed within a body of a subject.

14. The implantable device of claim 13, wherein the tissue layer includes a hydrogel encapsulating the plurality of pancreatic islet cells.

* * * * *